(12) United States Patent
Diehl et al.

(10) Patent No.: US 8,250,763 B2
(45) Date of Patent: Aug. 28, 2012

(54) BATTERY-OPERATED RAZOR

(75) Inventors: Martin Diehl, Bad Vilbel (DE); Ulrich Fandrey, Wetzlar (DE); Uwe Schaaf, Alsbach-Hahnlein (DE); Florina Winter, Schmitten (DE); Fred Schnak, Kronberg (DE)

(73) Assignee: The Gillette Company, Boston, MA (US)

( * ) Notice: Subject to any disclaimer, the term of this patent is extended or adjusted under 35 U.S.C. 154(b) by 0 days.

(21) Appl. No.: 12/707,683

(22) Filed: Feb. 18, 2010

(65) Prior Publication Data

US 2010/0173519 A1  Jul. 8, 2010

Related U.S. Application Data

(62) Division of application No. 11/115,885, filed on Apr. 27, 2005, now Pat. No. 7,694,419.

(51) Int. Cl.
*B26B 21/14* (2006.01)
(52) U.S. Cl. ............... 30/67; 30/66; 30/526; 30/529; 429/97; 429/100
(58) Field of Classification Search ............... 429/97, 429/100; 30/43, 44, 45, 91, 210, 32
See application file for complete search history.

(56) References Cited

U.S. PATENT DOCUMENTS

| | | |
|---|---|---|
| 1,180,686 A | 4/1916 | Allport |
| 1,187,103 A | 6/1916 | Sagebrecht |
| RE15,022 E | 1/1921 | Burgess |
| 1,393,858 A | 10/1921 | Wachtel |
| 1,514,314 A | 11/1924 | Douglas |
| 1,618,939 A | 2/1927 | Marth |
| 1,990,504 A | 2/1935 | Stimson |
| 2,234,972 A | 3/1941 | Lennan |
| 2,235,714 A | 3/1941 | Lennan |
| 2,310,409 A | 2/1943 | Ellman |
| 2,478,325 A | 8/1949 | Russell |
| 2,626,299 A | 1/1953 | Richards |
| 2,648,762 A | 8/1953 | Dunkelberger |
| 2,704,356 A | 3/1955 | Herterick |
| 2,951,108 A | 8/1960 | Woods |
| 2,963,598 A | 12/1960 | Kent |
| 2,993,948 A | 7/1961 | Vaclaw |

(Continued)

FOREIGN PATENT DOCUMENTS

CN 2087500 U 10/1991

(Continued)

OTHER PUBLICATIONS

Hoffman "Fundamentals of Annular Snap-Fit Joints." *Machine Design Fastening and Joining* Jan. 6, 2005, 4 pages.

(Continued)

*Primary Examiner* — Patrick Ryan
*Assistant Examiner* — Ben Lewis
(74) *Attorney, Agent, or Firm* — Fish & Richardson P.C.

(57) ABSTRACT

Battery operated appliances are provided. Some appliances include a housing defining a chamber having an interior wall, electronics within the chamber, a battery cover, and a closing system including (a) a first electrically conductive member secured to the battery cover, and (b) a second electrically conductive member secured to the interior wall of the housing and configured to engage the first electrically conductive member and thereby mechanically secure the battery cover to the housing while also establishing electrical contact between the first and second electrically conductive members.

19 Claims, 3 Drawing Sheets

U.S. PATENT DOCUMENTS

| | | |
|---|---|---|
| 3,070,748 A | 12/1962 | Worobey et al. |
| 3,104,405 A | 9/1963 | Perrinjaquet |
| 3,183,538 A | 5/1965 | Hubner |
| 3,346,748 A | 10/1967 | McNair |
| 3,358,309 A | 12/1967 | Richardson |
| 3,364,455 A | 1/1968 | Nodfelt |
| 3,549,920 A | 12/1970 | Tavel |
| 3,550,280 A | 12/1970 | Palm |
| 3,568,313 A | 3/1971 | Hutter |
| 3,602,217 A | 8/1971 | Felton |
| 3,609,632 A | 9/1971 | Vetter |
| 3,613,696 A | 10/1971 | Paule et al. |
| 3,623,481 A | 11/1971 | Curran |
| 3,636,627 A | 1/1972 | Tiffin |
| 3,685,080 A | 8/1972 | Hubner |
| 3,702,487 A | 11/1972 | Sung |
| 3,705,578 A | 12/1972 | Cutler et al. |
| 3,779,238 A | 12/1973 | Cutler et al. |
| 3,887,393 A | 6/1975 | La Rue, Jr. |
| 3,945,076 A | 3/1976 | Sung |
| 3,945,702 A | 3/1976 | Poliak et al. |
| 3,967,617 A | 7/1976 | Krolik |
| 4,004,344 A | 1/1977 | Gold et al. |
| 4,027,348 A | 6/1977 | Flowers et al. |
| 4,053,688 A | 10/1977 | Perkins et al. |
| 4,072,385 A | 2/1978 | Wallner |
| 4,103,694 A | 8/1978 | Burian et al. |
| 4,149,530 A | 4/1979 | Gow |
| 4,175,299 A | 11/1979 | Teague, Jr. et al. |
| 4,183,140 A | 1/1980 | Rieselman |
| 4,203,221 A | 5/1980 | Knopp et al. |
| 4,213,078 A | 7/1980 | Ferrell et al. |
| 4,213,471 A | 7/1980 | Burian et al. |
| 4,220,985 A | 9/1980 | Hukuba |
| 4,236,889 A | 12/1980 | Wright |
| 4,276,672 A | 7/1981 | Teague, Jr. et al. |
| 4,336,622 A | 6/1982 | Teague, Jr. et al. |
| 4,377,877 A | 3/1983 | O'Rourke |
| 4,390,225 A | 6/1983 | Coyne et al. |
| 4,398,238 A | 8/1983 | Nelson |
| 4,440,464 A | 4/1984 | Spinner |
| 4,447,749 A | 5/1984 | Reeb, Jr. et al. |
| 4,479,516 A | 10/1984 | Hunter |
| 4,495,551 A | 1/1985 | Foltz |
| 4,563,728 A | 1/1986 | Bruggeman et al. |
| 4,644,244 A | 2/1987 | Kittelson |
| 4,656,565 A | 4/1987 | Maglica |
| 4,669,452 A | 6/1987 | Osawa |
| 4,724,563 A | 2/1988 | Fry et al. |
| 4,751,452 A | 6/1988 | Kilmer et al. |
| 4,806,440 A | 2/1989 | Hahs, Jr. et al. |
| 4,835,410 A | 5/1989 | Bhagwat et al. |
| 4,845,795 A | 7/1989 | Crawford et al. |
| 4,913,133 A | 4/1990 | Tichy |
| 4,924,358 A | 5/1990 | Von Heck |
| 5,000,684 A | 3/1991 | Odrich |
| 5,006,073 A | 4/1991 | Mennona, Jr. |
| 5,007,169 A | 4/1991 | Motta |
| 5,033,150 A | 7/1991 | Gross et al. |
| 5,062,211 A | 11/1991 | Di Amico |
| 5,071,348 A | 12/1991 | Woog |
| 5,088,145 A | 2/1992 | Whitefield |
| 5,122,427 A | 6/1992 | Flowers et al. |
| 5,123,841 A | 6/1992 | Millner |
| 5,138,733 A | 8/1992 | Bock |
| 5,160,194 A | 11/1992 | Feldman |
| 5,165,131 A | 11/1992 | Staar |
| 5,234,355 A | 8/1993 | Sosinski et al. |
| 5,253,382 A | 10/1993 | Beny |
| 5,259,083 A | 11/1993 | Stansbury, Jr. |
| 5,267,579 A | 12/1993 | Bushberger |
| 5,283,921 A | 2/1994 | Ng |
| 5,299,354 A | 4/1994 | Metcalf et al. |
| 5,311,632 A | 5/1994 | Center |
| 5,344,317 A | 9/1994 | Pächer et al. |
| 5,353,460 A | 10/1994 | Bauman |
| 5,378,153 A | 1/1995 | Giuliani et al. |
| 5,421,726 A | 6/1995 | Okada |
| 5,435,033 A | 7/1995 | Millner |
| 5,438,726 A | 8/1995 | Leite |
| 5,445,900 A | 8/1995 | Miller, Jr. et al. |
| 5,471,695 A | 12/1995 | Aiyar |
| 5,476,729 A | 12/1995 | Miller, Jr. et al. |
| 5,493,747 A | 2/1996 | Inakagata et al. |
| 5,504,961 A | 4/1996 | Yang |
| 5,511,270 A | 4/1996 | Eliachar et al. |
| 5,524,312 A | 6/1996 | Tan et al. |
| 5,544,382 A | 8/1996 | Giuliani et al. |
| 5,544,415 A * | 8/1996 | Huang ............... 30/43.92 |
| 5,546,624 A | 8/1996 | Bock |
| 5,561,881 A | 10/1996 | Klinger et al. |
| 5,573,020 A | 11/1996 | Robinson |
| 5,590,434 A | 1/1997 | Imai |
| 5,601,359 A | 2/1997 | Sharrah et al. |
| 5,613,259 A | 3/1997 | Craft et al. |
| 5,617,602 A | 4/1997 | Okada |
| 5,622,192 A | 4/1997 | Chiou |
| 5,625,916 A | 5/1997 | McDougall |
| 5,640,979 A | 6/1997 | Trenary |
| 5,642,931 A | 7/1997 | Gappelberg |
| 5,651,157 A | 7/1997 | Hahn |
| 5,681,667 A | 10/1997 | Bunyea et al. |
| 5,706,541 A | 1/1998 | Gutelius et al. |
| 5,706,542 A | 1/1998 | Okada |
| 5,718,667 A | 2/1998 | Sugimoto et al. |
| 5,738,575 A | 4/1998 | Bock |
| 5,770,328 A | 6/1998 | Friedli et al. |
| 5,784,742 A | 7/1998 | Giuliani et al. |
| 5,784,743 A | 7/1998 | Shek |
| 5,787,908 A | 8/1998 | Robinson |
| 5,794,295 A | 8/1998 | Shen |
| 5,822,821 A | 10/1998 | Sham |
| 5,827,064 A | 10/1998 | Bock |
| RE35,941 E | 11/1998 | Stansbury, Jr. |
| 5,857,233 A | 1/1999 | Wynn |
| 5,901,397 A | 5/1999 | Häfele et al. |
| 5,919,585 A | 7/1999 | Wheeler et al. |
| 5,930,858 A | 8/1999 | Jung |
| 5,944,033 A | 8/1999 | Robinson |
| 5,947,912 A | 9/1999 | Montagnino |
| 5,980,248 A | 11/1999 | Kusakabe et al. |
| 5,987,681 A | 11/1999 | Hahn et al. |
| 6,000,083 A | 12/1999 | Blaustein et al. |
| 6,050,818 A | 4/2000 | Boland et al. |
| 6,058,542 A | 5/2000 | Lo |
| 6,092,252 A | 7/2000 | Fischer et al. |
| 6,138,310 A | 10/2000 | Porper et al. |
| 6,139,359 A | 10/2000 | Fuhreck et al. |
| 6,140,723 A | 10/2000 | Matsui et al. |
| 6,178,579 B1 | 1/2001 | Blaustein et al. |
| 6,189,693 B1 | 2/2001 | Blaustein et al. |
| 6,202,242 B1 | 3/2001 | Salmon et al. |
| 6,209,164 B1 | 4/2001 | Sato |
| 6,218,042 B1 | 4/2001 | Naudet et al. |
| 6,226,068 B1 | 5/2001 | Arcykiewicz et al. |
| 6,334,232 B1 | 1/2002 | Sato |
| 6,347,425 B1 | 2/2002 | Fattori et al. |
| 6,360,395 B2 | 3/2002 | Blaustein et al. |
| 6,363,565 B1 | 4/2002 | Paffrath |
| 6,401,288 B1 | 6/2002 | Porper et al. |
| 6,685,493 B2 | 2/2004 | Birkenmaier et al. |
| 6,725,490 B2 | 4/2004 | Blaustein et al. |
| 6,777,890 B1 | 8/2004 | Huang |
| 6,802,097 B2 | 10/2004 | Häfliger et al. |
| 6,920,659 B2 | 7/2005 | Cacka et al. |
| 6,966,093 B2 | 11/2005 | Eliav et al. |
| 7,003,839 B2 | 2/2006 | Häfliger et al. |
| 7,086,886 B2 | 8/2006 | Thurston |
| 7,104,826 B2 | 9/2006 | Zahlit et al. |
| 7,137,163 B2 | 11/2006 | Gatzemeyer et al. |
| 7,140,058 B2 | 11/2006 | Gatzemeyer et al. |
| 7,240,390 B2 | 7/2007 | Pfenniger et al. |
| 7,241,413 B2 | 7/2007 | Pfenniger et al. |
| 7,254,858 B2 | 8/2007 | Häfliger et al. |
| 7,261,851 B2 | 8/2007 | Häfliger et al. |
| 7,556,320 B2 | 7/2009 | Häfliger et al. |
| 7,637,014 B2 | 12/2009 | Schnak et al. |

| | | |
|---|---|---|
| 7,748,071 B2 | 7/2010 | Hafliger et al. |
| 7,810,243 B2 | 10/2010 | Schnak et al. |
| 8,015,649 B2 | 9/2011 | Häfliger et al. |
| 2002/0032941 A1 | 3/2002 | Blaustein et al. |
| 2002/0045093 A1 | 4/2002 | Imamura et al. |
| 2002/0078514 A1 | 6/2002 | Blaustein et al. |
| 2002/0124333 A1 | 9/2002 | Häfliger et al. |
| 2002/0127468 A1 | 9/2002 | Wani et al. |
| 2002/0178519 A1 | 12/2002 | Zarlengo |
| 2003/0013338 A1* | 1/2003 | Birkenmaier et al. ........ 439/332 |
| 2003/0196283 A1 | 10/2003 | Eliav et al. |
| 2003/0226223 A1 | 12/2003 | Chan |
| 2004/0013938 A1 | 1/2004 | Murashige et al. |
| 2004/0095759 A1 | 5/2004 | Koch et al. |
| 2005/0011026 A1 | 1/2005 | Häfliger et al. |
| 2005/0172493 A1 | 8/2005 | Fischer et al. |
| 2006/0026780 A1 | 2/2006 | Häfliger et al. |
| 2006/0032512 A1 | 2/2006 | Kress et al. |
| 2006/0156496 A1 | 7/2006 | Häfliger et al. |
| 2007/0256259 A1 | 11/2007 | Häfliger et al. |
| 2009/0126132 A1 | 5/2009 | Häfliger et al. |
| 2010/0242194 A1 | 9/2010 | Häfliger et al. |
| 2011/0289703 A1 | 12/2011 | Häfliger et al. |

FOREIGN PATENT DOCUMENTS

| | | |
|---|---|---|
| DE | 2820437 A1 | 7/1979 |
| DE | 4336088 C * | 1/1995 |
| DE | 10005738 A1 | 8/2001 |
| EP | 0 704 180 A1 | 4/1996 |
| GB | 2 042 787 A | 9/1980 |
| GB | 2 250 428 A | 6/1992 |
| JP | 03222905 A2 | 10/1991 |
| JP | 8117258 | 5/1996 |
| WO | WO 79/01163 | 12/1979 |
| WO | WO 01/82825 A1 | 11/2001 |

OTHER PUBLICATIONS

Rotheiser Joining of Plastics Handbook for Designers and Engineers, 2nd Edition, Hanser Publishers, Munich © 2004, Snap Fits, 5 pages.

Tres, Designing Plastic Parts for Assembly, 3rd Edition, Hanser Publishers, Munich © 1998, Snap Fitting, 3 pages.

\* cited by examiner

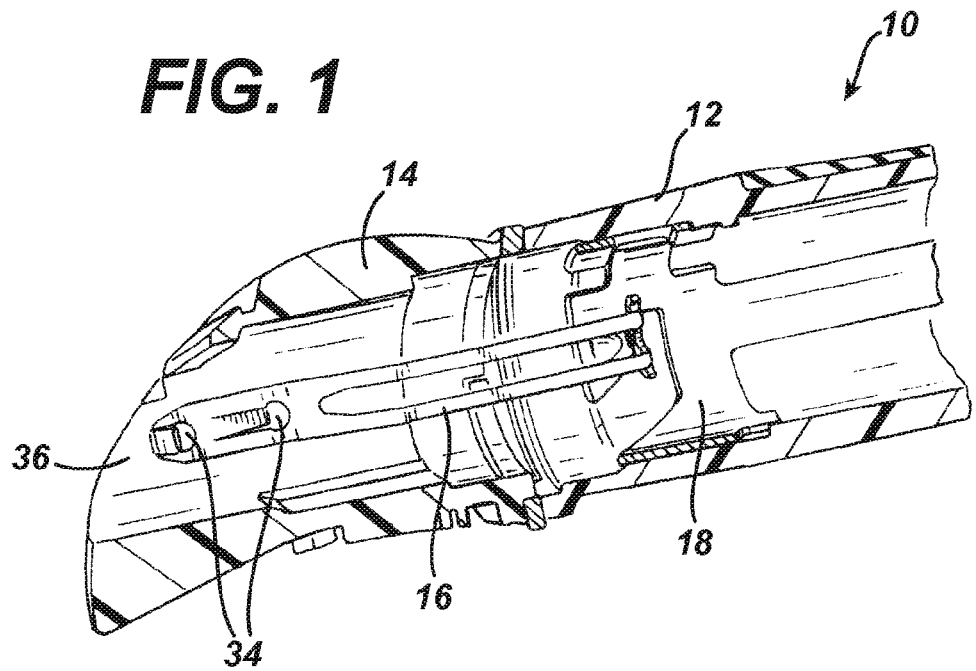
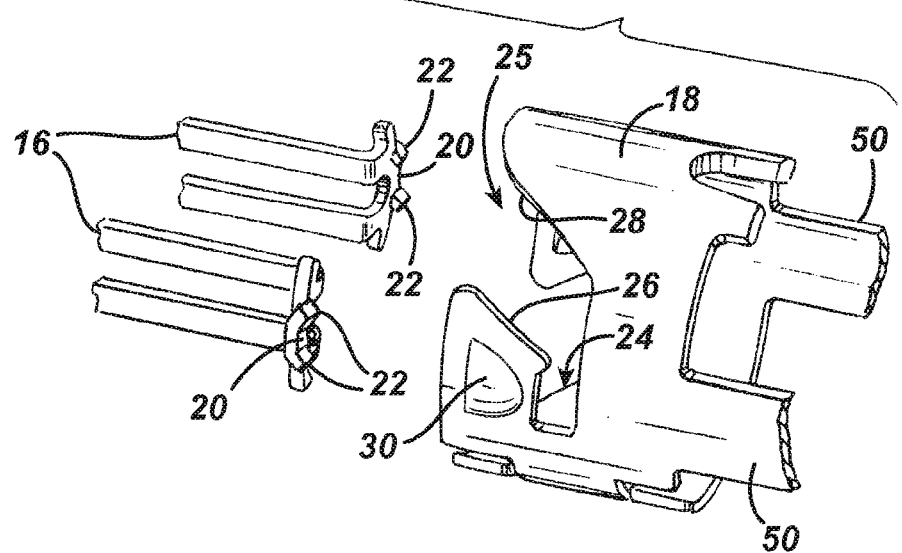

BATTERY-OPERATED RAZOR

CROSS REFERENCE TO RELATED APPLICATION

This application is a continuation of U.S. patent application Ser. No. 11/115,885 filed Apr. 27, 2005, now U.S. Pat. No. 7,694,419.

TECHNICAL FIELD

This invention relates to battery-operated appliances, such as personal care appliances, and more particularly to battery case covers for such appliances.

BACKGROUND

In many small battery-operated devices, the batteries are replaceable by the user, and are inserted and removed from a battery compartment through an opening having a cover. It is necessary to mechanically secure the cover in place, so that the batteries do not fall out and the cover is not lost. It is also necessary to make electrical contact between the batteries and the electrical circuit within the device.

SUMMARY

The present invention provides a simple, efficient mechanism for both securing a battery cover to the housing of a small appliance and at the same time providing a high reliability electrical contact between the battery and electronics of the appliance. Preferred closing systems include very few parts and thus are easy and economical to manufacture and assemble. Moreover, some preferred closing systems are suitable for use with small, space saving housing designs and/or designs that includes non-linear seam lines between the battery cover and housing.

In one aspect, the invention features a battery operated appliance including a housing defining a chamber having an interior wall, electronics within the chamber, a battery cover, the battery cover and/or the housing being configured to contain one or more batteries, and a closing system. The closing system includes a first electrically conductive member secured to the battery cover, and a second electrically conductive member secured to the interior wall of the housing and configured to engage the first electrically conductive member and thereby mechanically secure the battery cover to the housing while also establishing electrical contact between the first and second electrically conductive members.

Some implementations may include one or more of the following features. The first and second electrically conductive members may be configured to engage each other by rotation of the battery cover relative to the housing. For example, the second electrically conductive member may include a circumferentially extending slot having an open end and the first electrically conductive member may include a hook configured to slide into the slot through the open end during rotation. The interior wall of the housing may be generally cylindrical, and/or outer surfaces of the housing and battery cover may be generally cylindrical. By "generally cylindrical" we mean that the housing and battery cover may each include non-cylindrical elements, e.g., ridges, protrusions, or recesses, and/or may include regions along its length that are not cylindrical.

The first electrically conductive member may include a spring element configured to apply an axial force between the housing and battery cover when the first and second electrically conductive members are engaged. The first electrically conductive member includes two or more spring elements, and each spring element may provide an electrical contact between the first and second electrically conductive members.

The first and second electrically conductive members may be secured to the battery cover and housing, respectively, by a snap fit. For example, the second electrically conductive member may include a spring portion that is compressed prior to insertion into the housing and that engages the interior wall of the housing with a radial spring force. The spring portion may be generally ring-shaped. The second electrically conductive element may also include one or more undercuts configured to engage corresponding undercuts on the interior wall of the housing.

The second electrically conductive member may include a portion configured to make electrical contact with an electronic sub-assembly of the appliance, e.g., one or more power rails. Each power rail may include a clip constructed to engage the sub-assembly, and this engagement may mechanically secure the second electrically conductive member to the sub-assembly.

The second electrically conductive member may include engagement regions configured for mechanical engagement with corresponding regions on the first electrically conductive member, and each undercut on the second electrically conductive element may be generally axially aligned with one of the engagement regions.

The appliance may be, for example, a power toothbrush or a razor having an electrically-activated function. Thus, the electronics may be configured to drive a toothbrush head or to drive a vibrating function of a razor for wet shaving.

In another aspect, the invention features a battery operated appliance, such as a razor or power toothbrush, including a generally cylindrical housing defining a chamber having a generally cylindrical interior wall, electronics within the chamber, a generally cylindrical battery cover, the battery cover and/or the housing being configured to contain one or more batteries, and a closing system including a first electrically conductive member secured to the battery cover, and a second electrically conductive member secured to the interior wall of the housing and configured to engage the first electrically conductive member during rotation of the battery cover relative to the housing, thereby mechanically securing the battery cover to the housing while also establishing electrical contact between the first and second electrically conductive members.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a perspective view of a closing system according to one embodiment of the invention, with the front portion of the housing and battery cover cut away to show the internal components.

FIG. 2 is an enlarged exploded perspective view showing two components of the closing system of FIG. 1.

Like reference symbols in the various drawings indicate like elements.

DETAILED DESCRIPTION

Figure 3:
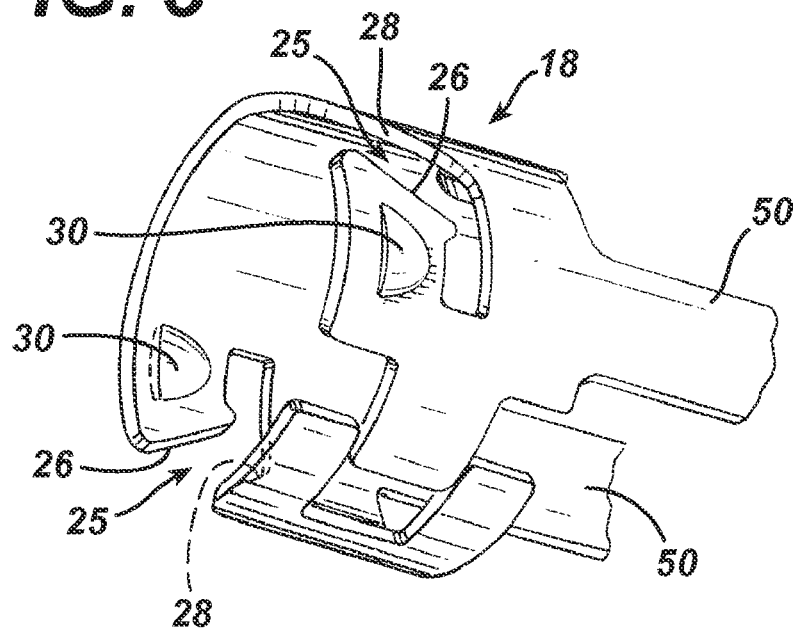
FIG. 3 is an enlarged perspective view of one of the components shown in FIG. 2, rotated to a different position.

Referring to FIG. 1, a battery powered device 10 includes a cylindrical housing 12 and a generally cylindrical battery cover 14. The battery cover 14 is mounted on the housing 12 by the connection of one or more metal spring element(s) 16 to a generally cylindrical metal receiving part 18. Spring elements 16 and receiving part 18 will now be discussed in detail, with reference to FIGS. 2-4.

Figure 4:
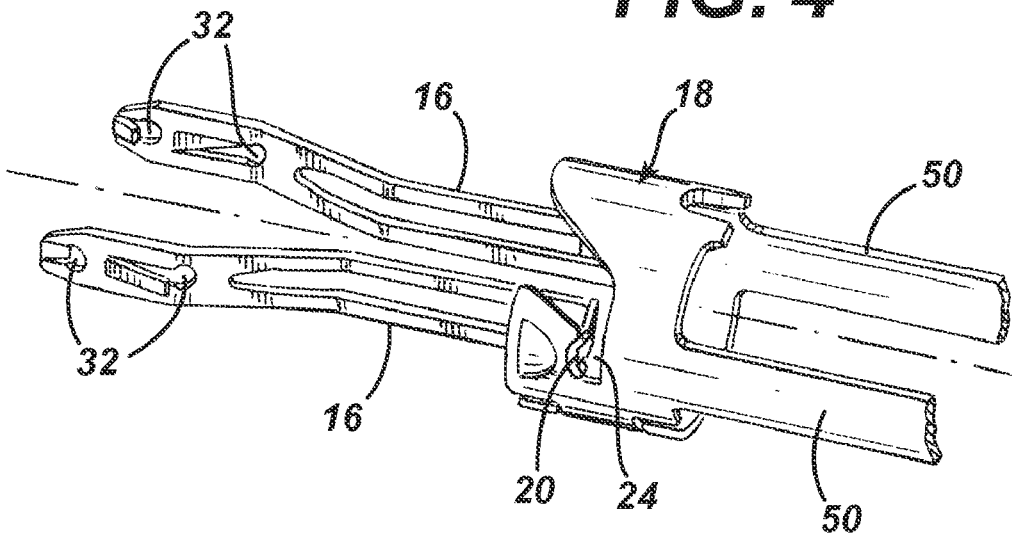
FIG. 4 is a perspective view showing the components of FIG. 2 in an assembled state.

Two spring elements are shown in FIGS. 2-4. However, more or fewer may be used, as will be understood by those skilled in the art. Generally, the more spring elements used, the higher the electrical reliability and the stronger the connection between the battery cover and the housing.

Figure 5:
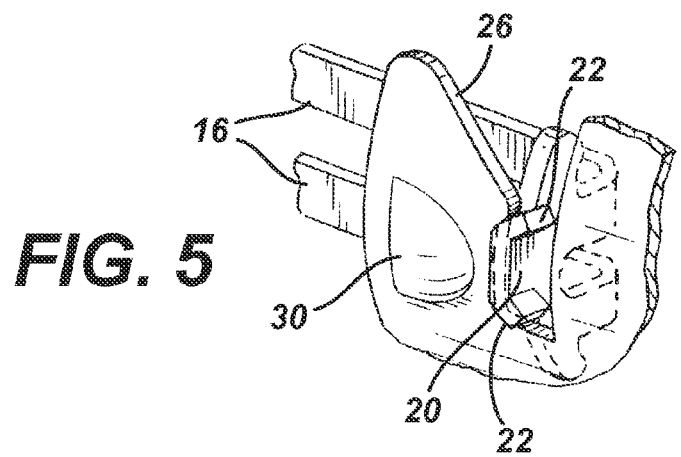
FIG. 5 is an enlarged detail view of a portion of the assembly shown in FIG. 4.

Referring to FIG. 2, each spring element 16 has a hook 20 at one end. Each hook includes one or more protrusions 22. The hooks are constructed to be received and retained in corresponding slots 24 in the receiving part 18, as shown in FIGS. 1, 4 and 5, with protrusions 22 facilitating insertion, removal, and retention of the hooks. Each slot 24 includes a lead-in 25 having angled walls 26, 28, to guide the hook into the slot as the battery cover is rotated relative to the housing. The engagement of the hooks in the slots provides a secure, twist-on mechanical connection of the battery cover to the housing.

The spring elements are designed to apply a spring force axially along the long axis of the housing. In the embodiment shown, the S-shaped profile of the springs (FIG. 4), along with stretching of the springs during operation, generates this spring force. Thus, as the spring element moves into the slot it is stretched, pulling the battery cover and housing together. This resilient engagement of the battery cover with the housing compensates for non-linear seam lines between the battery cover and housing and other geometry issues such as tolerances.

The spring members and the receiving part are both made of metal, and thus engagement of the hooks with the slots also provides electrical contact between the spring members and the receiving part. The receiving part is in turn in electrical contact with circuitry of the device, as will be discussed below, and the battery is in contact with the spring members, and thus contact of the spring members and electrical part ultimately results in contact between the battery and the circuitry of the device. Accordingly, the spring function of the spring elements is also advantageous because it serves to provide solid and reliable electrical contact between the spring elements and the receiving part.

The spring members and receiving part are easily assembled into the device. The spring members are retained permanently on the battery cover by press-fitting protrusions 34 on the inner wall 36 of the battery cover into slotted openings 32 on each spring member (see FIGS. 1 and 4). The receiving part 18 is retained permanently in the housing 12 by engagement of undercuts 30 on the receiving part with corresponding undercuts (not shown) on the inner wall of housing 12. The engagement of the receiving part and housing is achieved by a spring action of the receiving part. The receiving part has a diameter that, in an uncompressed state, is greater than the inner diameter of the housing 12. During assembly, the receiving part is compressed until its outer diameter, including undercuts 30, is less than the inner diameter of the housing 12. The receiving part is then inserted into the housing, and allowed to spring back to its normal, uncompressed diameter. If desired, the receiving part can be heated, e.g., by inductive heating, prior to insertion into the housing, so that the hot undercuts will dig themselves into the plastic of the housing as the receiving part springs back to its uncompressed state.

Preferably, the undercuts 30 are relatively close to the slots 24, and more preferably are axially aligned therewith, as shown. Alignment of the undercuts with the slots allows forces applied to the slot during and subsequent to closing to be transmitted directly to the attachment points of the receiving part (the undercuts). This arrangement provides an assembly that is very rigid and that is relatively insensitive to tolerances.

Figure 6:
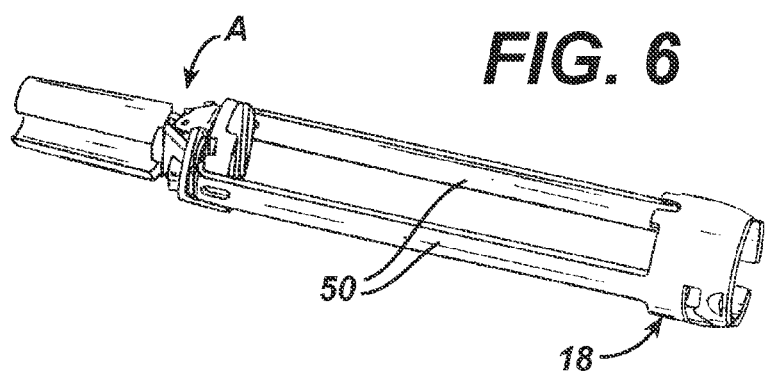
FIG. 6 is a perspective view showing one of the components of FIG. 2 assembled with a further sub-assembly.
Figure 7:
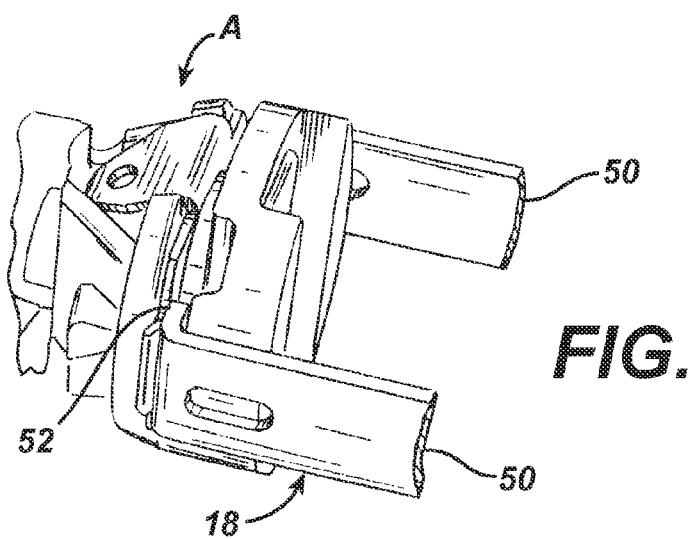
FIG. 7 is an enlarged detail view of a portion of the assembly shown in FIG. 6.

Referring now to FIGS. 6 and 7, the receiving part 18 may be used to make electrical connection with a sub-assembly A, for instance a device that causes the appliance to vibrate. In this case, the receiving part 18 includes arms 50 which act as power rails, providing an electrical connection to sub-assembly A. Each arm 50 includes a terminal hook 52, which engages a corresponding structure on sub-assembly A (FIG. 7), typically by press-fitting or snapping the hooks into a groove or recess of the sub-assembly. As is the case with the engagement of the spring elements with the receiving part, discussed above, the engagement of the hooks 52 with the sub-assembly A serves two functions: (a) mechanically securing the sub-assembly in place, and (b) providing electrical connection between the arms 50 (and ultimately the battery) and the sub-assembly A. This dual functionality reduces the number of parts required, saves space, and simplifies assembly of the appliance.

A number of embodiments of the invention have been described. Nevertheless, it will be understood that various modifications may be made without departing from the spirit and scope of the invention. For example, while razors and toothbrushes are mentioned above, the closing systems discussed herein may be used with many other types of appliances, for example flashlights, battery powered scrubbrushes, and cameras. Moreover, while in the embodiments shown in the figures, the battery cover carries a "male" engagement member and the housing carries a corresponding "female" engagement member, this arrangement may be reversed so that the battery cover carries the female engagement member and the housing carries the male engagement member, or other types of cooperative engagement may be used. Accordingly, other embodiments are within the scope of the following claims.

What is claimed is:

1. A battery operated razor comprising
a housing defining a chamber having an interior wall,
electronics within the chamber,
a battery cover, the battery cover and/or the housing being configured to contain one or more batteries, and
a closing system, including a first electrically conductive member secured to the battery cover, and a second electrically conductive member secured to the interior wall of the housing and configured to engage the first electrically conductive member during rotation of the battery cover relative to the housing, thereby mechanically securing the battery cover to the housing while also establishing electrical contact between the first and second electrically conductive members,
wherein the first electrically conductive member includes one or more circumferentially extending slots.

2. The razor of claim 1 wherein the circumferentially extending slot has an open end and the second electrically conductive member includes a hook configured to slide into the slot through the open end during rotation.

3. The razor of claim 2 wherein the open end of the slot includes a lead-in configured to guide insertion of the hook into the slot.

4. The razor of claim 1 or 2 wherein the interior wall of the housing is generally cylindrical.

5. The razor of claim 1 wherein outer surfaces of the housing and battery cover are generally cylindrical.

6. The razor of claim 1 wherein the second electrically conductive member comprises a spring element configured to apply an axial force between the housing and battery cover when the first and second electrically conductive members are engaged.

7. The razor of claim 6 wherein the second electrically conductive member includes two or more spring elements.

8. The razor of claim 6 wherein the spring element provides an electrical contact between the first and second electrically conductive members.

9. The razor of claim 1 wherein the first and second electrically conductive members are secured to the battery cover and housing, respectively, by a snap fit.

10. The razor of claim 1 wherein the second electrically conductive element includes one or more undercuts configured to engage corresponding undercuts on the interior wall of the housing.

11. The razor of claim 10 wherein the second electrically conductive member includes engagement regions configured for mechanical engagement with corresponding regions on the first electrically conductive member, and each undercut on the second electrically conductive element is generally axially aligned with one of the engagement regions.

12. The razor of claim 1 wherein the second electrically conductive member includes a portion configured to make electrical contact with an electronic sub-assembly of the razor.

13. The razor of claim 12 wherein the portion comprises one or more power rails.

14. The razor of claim 13 wherein each power rail includes a clip constructed to engage the sub-assembly.

15. The razor of claim 14 wherein each clip is configured to mechanically secure the second electrically conductive member to the sub-assembly.

16. The razor of claim 1 wherein the electronics are configured to drive a vibrating function of the razor.

17. The razor of claim 1 wherein the housing comprises the handle of a razor.

18. The razor of claim 1 wherein the first electrically conductive member comprises one or more undercuts configured to engage corresponding undercuts on the battery cover.

19. The razor of claim 18 wherein one of the one or more circumferentially extending slots is relatively close to and generally axially aligned with at least one of the undercuts.

* * * * *

UNITED STATES PATENT AND TRADEMARK OFFICE
CERTIFICATE OF CORRECTION

PATENT NO. : 8,250,763 B2  
APPLICATION NO. : 12/707683  
DATED : August 28, 2012  
INVENTOR(S) : Martin Diehl et al.

Page 1 of 1

It is certified that error appears in the above-identified patent and that said Letters Patent is hereby corrected as shown below:

First Page, Col. 1, (Related U.S. Application data), Delete "Division" and insert --Continuation--, therefor.

Signed and Sealed this
Twentieth Day of November, 2012

David J. Kappos
*Director of the United States Patent and Trademark Office*